US008785206B2

United States Patent
Hyde et al.

(10) Patent No.: US 8,785,206 B2
(45) Date of Patent: *Jul. 22, 2014

(54) DRINKING VESSELS AND RELATED SYSTEMS AND METHODS

(71) Applicant: Searete LLC, Bellevue, WA (US)

(72) Inventors: Roderick A. Hyde, Redmond, WA (US); Muriel Y. Ishikawa, Livermore, CA (US); Jordin T. Kare, Seattle, WA (US); Eric C. Leuthardt, St. Louis, MO (US); Clarence T. Tegreene, Mercer Island, WA (US); Lowell L. Wood, Bellevue, WA (US); Victoria Y. H. Wood, Livermore, CA (US)

(73) Assignee: The Invention Science Fund I, LLC, Bellevue, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/763,313

(22) Filed: Feb. 8, 2013

(65) Prior Publication Data

US 2013/0151168 A1  Jun. 13, 2013

Related U.S. Application Data

(62) Division of application No. 12/462,051, filed on Jul. 28, 2009, now Pat. No. 8,398,920.

(51) Int. Cl.
*G01N 33/14* (2006.01)
*G01N 33/00* (2006.01)

(52) U.S. Cl.
CPC ............ *G01N 33/0004* (2013.01); *G01N 33/14* (2013.01)
USPC .............. 436/132; 436/43; 422/68.1; 422/50; 422/83; 422/84; 422/62; 702/24

(58) Field of Classification Search
CPC .................................................. G01N 33/0004
USPC ........... 422/68.1, 50, 83, 84, 62; 436/43, 132; 702/22–24
See application file for complete search history.

(56) References Cited

U.S. PATENT DOCUMENTS

| 3,896,659 A | 7/1975 | Goodman |
| 5,478,987 A | 12/1995 | Morita |
| 7,218,236 B2 | 5/2007 | Mobley et al. |
| 2002/0119513 A1 | 8/2002 | Alocilja et al. |
| 2007/0092770 A1* | 4/2007 | Obata et al. ............... 429/22 |
| 2011/0029255 A1 | 2/2011 | Hyde et al. |

OTHER PUBLICATIONS

A Versatile Acoustic Waveguide Sensor for Liquids Based on Multiple Mode Conversion at Solid Liquid Interfaces, G. Lindner et al., 2006 IEEE Ultrasonics Symposium (pp. 1181-1184).

* cited by examiner

*Primary Examiner* — Lyle Alexander
(74) *Attorney, Agent, or Firm* — Dorsey & Whitney LLP

(57) ABSTRACT

Embodiments disclosed herein are directed to systems configured to determine an amount of alcohol in an alcohol-containing liquid discharged from a drinking vessel or an amount of the alcohol-containing liquid discharged from the drinking vessel, drinking vessels configured to measure alcohol content or other property of an alcohol-containing liquid held therein, other related components such as mat devices that facilitate determining the amount, and related methods. The systems, drinking vessels, and methods disclosed herein facilitate determination of an amount of alcohol in an alcohol-containing liquid discharged from a drinking vessel or an amount of alcohol-containing liquid discharged from the drinking vessel, which may be indicative of an amount of alcohol consumed by a drinker.

40 Claims, 10 Drawing Sheets

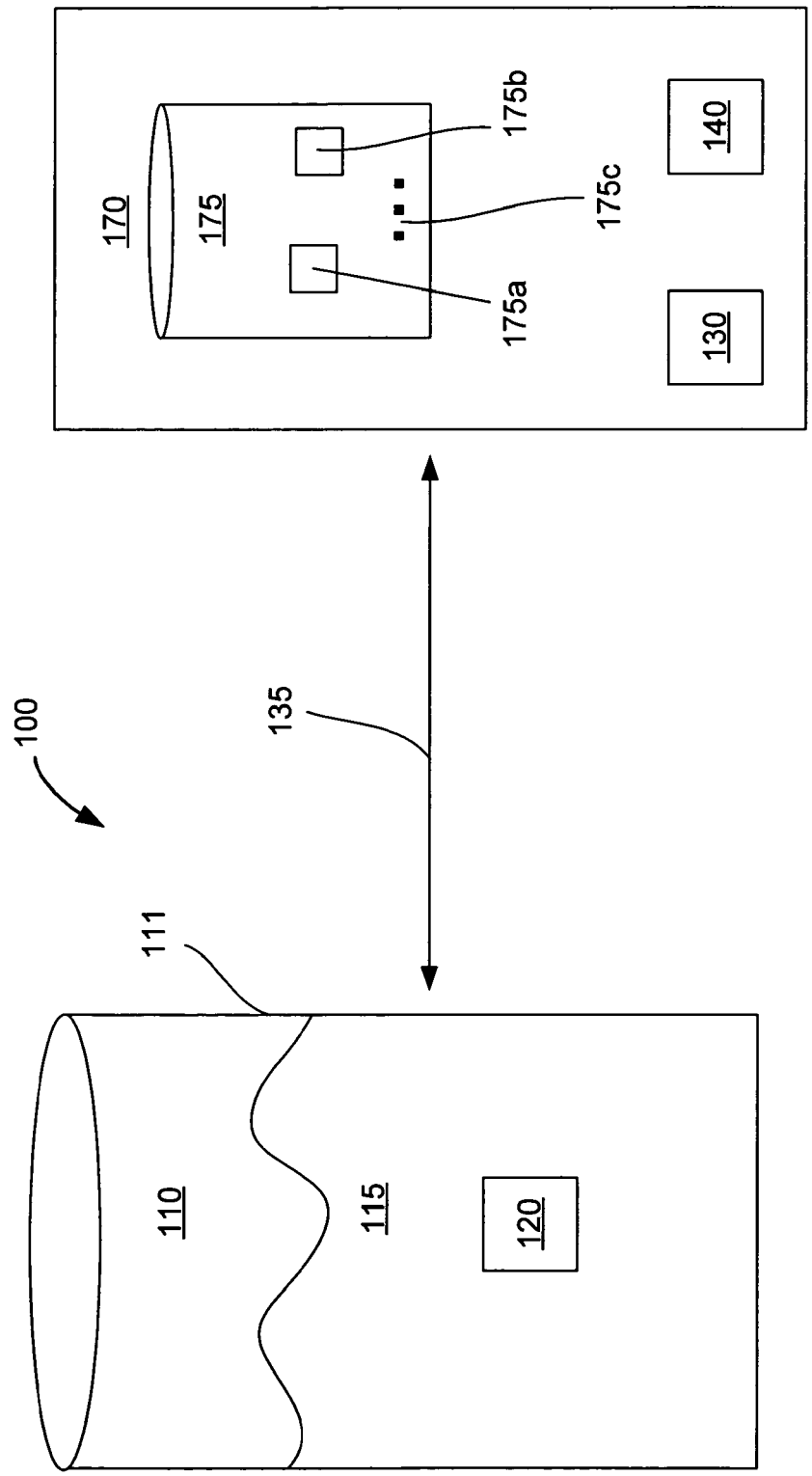

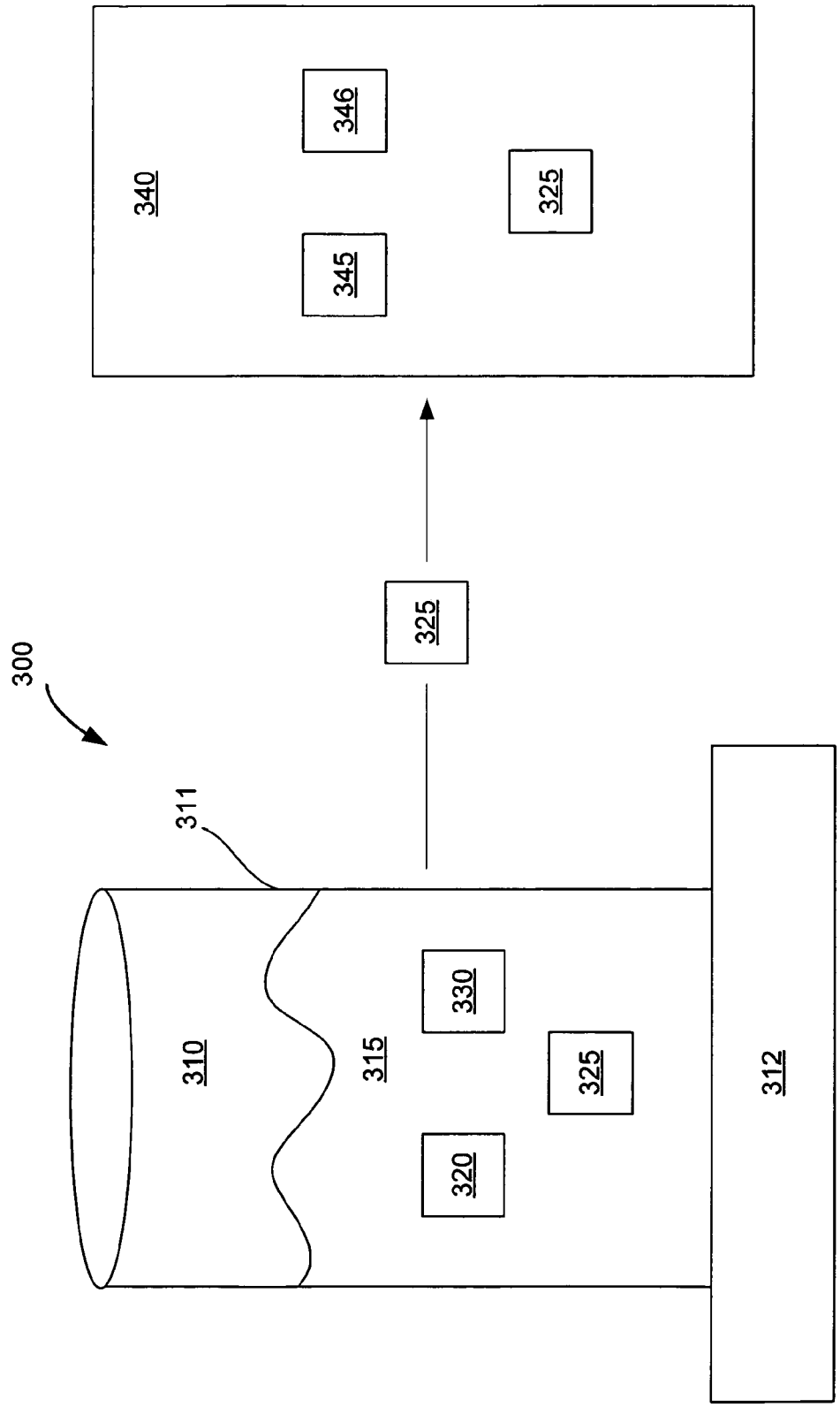

DRINKING VESSELS AND RELATED SYSTEMS AND METHODS

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

For purposes of the USPTO extra-statutory requirements, the present application constitutes a divisional of U.S. patent application Ser. No. 12/462,051, entitled DRINKING VESSELS AND RELATED SYSTEMS AND METHODS, naming Roderick A. Hyde, Muriel Y. Ishikawa, Jordin T. Kare, Eric C. Leuthardt, Clarence T. Tegreene, Lowell L. Wood Jr., and Victoria Y. H. Wood as inventors, filed 28 Jul. 2009, now U.S. Pat. No. 8,398,920.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In an embodiment, a drinking vessel includes a vessel body configured to hold an alcohol-containing liquid and a sensing system associated with the vessel body. The sensing system includes an alcohol-content sensor configured to determine an alcohol content of the alcohol-containing liquid.

In an embodiment, a drinking vessel includes a vessel body configured to hold an alcohol-containing liquid and a reporting device associated with the vessel body. The reporting device is configured to report information at least related to an amount of alcohol in the alcohol-containing liquid that has been discharged from the vessel body.

In an embodiment, a mat device includes a mat body configured to support a drinking vessel thereon that contains an alcohol-containing liquid and a processor associated with the mat body. The processor is configured to determine an amount of alcohol in the alcohol-containing liquid discharged from the vessel body.

In an embodiment, a system includes a drinking vessel including a vessel body configured to hold an alcohol-containing liquid, at least one sensing device, a processor, and a reporting device. The at least one sensing device is configured to sense at least one characteristic of the alcohol-containing liquid. The processor is configured to determine an amount of alcohol in the alcohol-containing liquid discharged from the vessel body or the alcohol-containing liquid discharged from the vessel body based, at least in part, on the at least one characteristic. The reporting device is configured to report the amount determined by the processor.

In an embodiment, a method includes sensing, with at least one sensing device, at least one characteristic related to an amount of alcohol in an alcohol-containing liquid that is discharged from a drinking vessel. The method further includes reporting information associated with the at least one characteristic.

In an embodiment, a system includes an alcohol-sensing system, a reporting device coupled to the alcohol-sensing system, and at least one device. The alcohol-sensing system is configured to determine at least one characteristic related to an amount of alcohol in an alcohol-containing liquid that has been discharged from a drinking vessel and generate alcohol-consumption information based at least partially on the at least one characteristic. The reporting device is configured to report alcohol-consumption information indicating that a specific amount of alcohol in the alcohol-containing liquid has been discharged from the drinking vessel. The at least one device includes a receiver configured to receive the alcohol-consumption information from the reporting device and, in response thereto, at least partially change a mode of operation thereof.

In an embodiment, a method includes, at one or more devices, receiving information related to an amount of alcohol in an alcohol-containing liquid discharged from a drinking vessel. The method further includes, in response to the receiving the information, changing a mode of operation of the one or more devices.

In an embodiment, a method includes receiving electronic information related to an amount of alcohol in an alcohol-containing liquid discharged from a drinking vessel. The method further includes, in response to the receiving the electronic information, notifying at least one of a third party or at least one device with information related to the received information.

The foregoing is a summary and thus may contain simplifications, generalizations, inclusions, and/or omissions of detail; consequently, the reader will appreciate that the summary is illustrative only and is NOT intended to be in any way limiting. Other aspects, features, and advantages of the devices and/or processes and/or other subject matter described herein will become apparent after reading the teachings set forth herein.

BRIEF DESCRIPTION OF THE FIGURES

FIG. 1D is a functional block diagram of another embodiment of the system shown in FIG. 1A.

FIG. 3 is a functional block diagram of a system including at least one device that changes a mode of operation thereof in response to receiving information related to an amount of alcohol consumed by a drinker.

DETAILED DESCRIPTION

Figure 1A:
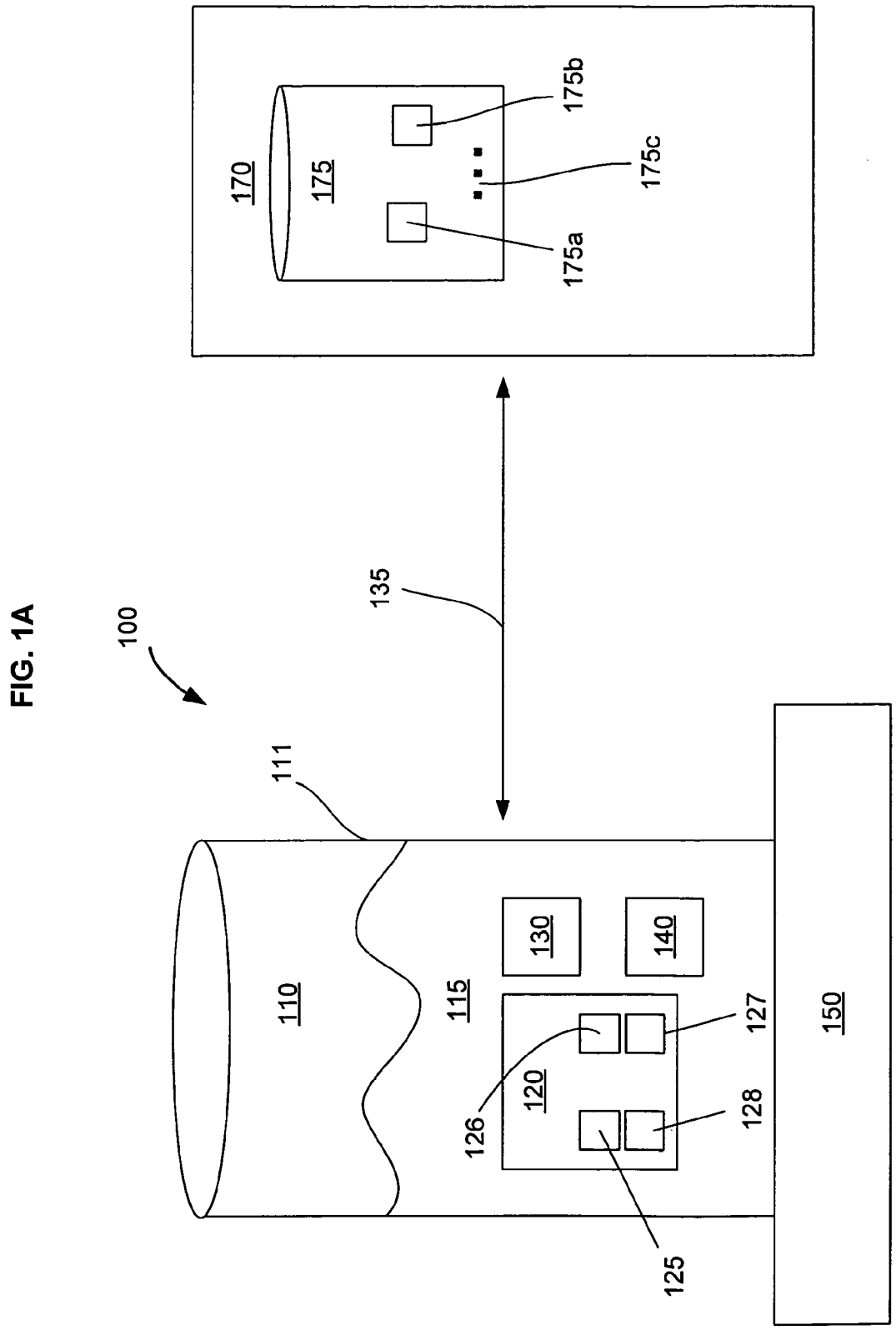
FIG. 1A is a functional block diagram of an embodiment of a system including a drinking vessel that holds an alcohol-containing liquid and various sensor and other components that are configured to determine an amount of alcohol or an amount of alcohol-containing liquid discharged from the drinking vessel.

Embodiments disclosed herein are directed to systems configured to determine an amount of alcohol in an alcohol-containing liquid discharged from a drinking vessel or an amount of the alcohol-containing liquid discharged from the drinking vessel, drinking vessels configured to measure alcohol content or other property of an alcohol-containing liquid held therein, other related components such as mat devices that facilitate determining the amount, and related methods. The systems, drinking vessels, and methods disclosed herein facilitate determination of an amount of alcohol in an alcohol-containing liquid discharged from a drinking vessel or an amount of alcohol-containing liquid discharged from the drinking vessel, which may be indicative of an amount of alcohol consumed by a drinker.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be strictly limiting. Other embodiments may be utilized, and other changes may be made, without departing from the spirit or scope of the subject matter presented herein.

FIG. 1A is a functional block diagram of an embodiment of a system 100 including a drinking vessel that holds an alcohol-containing liquid and various sensor and other components that are configured to determine an amount of alcohol or an amount of alcohol-containing liquid discharged from the drinking vessel, which may be indicative of the amount of alcohol consumed by a drinker. The system 100 includes a drinking vessel 110 that includes a vessel body 111. The drinking vessel 110 is configured to hold an amount of alcohol-containing liquid 115, which may be, for example, any suitable alcohol-containing liquid such as beer, wine, cocktail, or hard liquor. The drinking vessel 110 may be a glass, cup, mug, can, pitcher, or any other suitable drinking vessel that may hold alcohol-containing liquid. Further, the vessel body 111 may comprise plastic, glass, paper, or various metals, such as aluminum that are suitable to define the drinking vessel 110. It will be appreciated that the material comprising the vessel body 111 should be of a type that is sufficiently safe for the alcohol-containing liquid 115 to subsequently be consumed by a human being.

The drinking vessel 110 is associated with a sensing sub-system 120 configured to sense at least one characteristic of the alcohol-containing liquid 115 related to an amount of alcohol in or alcohol content of the alcohol-containing liquid 115, such as mass, weight, volume, one or more electrical properties, one or more acoustic properties, one more dielectric properties, or another suitable characteristic of the alcohol-containing liquid 115. The drinking vessel 110 may be further associated with a processor 130 that is operably coupled to the sensing sub-system 120 and configured to determine the amount of alcohol in the alcohol-containing liquid 115 discharged from the vessel body 111 or the amount of the alcohol-containing liquid 115 discharged from the vessel body 111 based on the at least one characteristic sensed by the sensing sub-system 120. The drinking vessel 110 may be further associated with a reporting device 140 configured to report the amount of alcohol determined by the processor 130. In an embodiment, the processor 130 may be configured to repetitively determine the amount of alcohol based on the at least one sensed characteristic.

It will be appreciated that although not explicitly shown in the figures, the various elements of the system 100 may be physically coupled or at least operably coupled to each other as circumstances warrant. It will also be appreciated that although FIG. 1A shows that drinking vessel 110 is associated with the sensor sub-system 120, the processor 130, and the reporting device 140, in an embodiment, the drinking vessel 110 may have a subset of one or two of these devices associated with it.

In an embodiment, the sensing sub-system 120, the processor 130, and the reporting device 140 may be integrated with or embedded within the vessel body 111. In other embodiments, all of these elements or a subset thereof may be attached to or mounted to a surface of vessel body 111 by a suitable adhesive, an attachment strap, or any other suitable attachment technique. In still additional embodiments to be described in more detail to follow, all of these elements or a subset thereof may not be integrated with or attached to drinking vessel 110, but rather may be integrated with or attached to other elements of the system 100.

In an embodiment, the drinking vessel 110 may be associated with a mat device 150 or other base device. In such an embodiment, the mat device 150 may be configured to support the drinking vessel 110 thereon as will be explained in more detail to follow. In addition, as will be described in more detail to follow, the sensing sub-system 120, the processor 130, and the reporting device 140 or a subset thereof may be incorporated with the mat device 150. Accordingly, any discussion herein relating to the sensing sub-system 120, the processor 130, and the reporting device 140 while incorporated with the drinking vessel 110 also applies when the sensing sub-system 120, the processor 130, or the reporting device 140 are incorporated with the mat device 150.

In one or more embodiments, the system 100 may further include a computer 170. The computer 170 may be any suitable computing device such as, for example, a phone, a desktop computer, a laptop computer, a personal data assistant ("PDA"), or a portable computing device. The computing device may include memory circuitry, which may be any suitable non-volatile memory such as database 175. The database 175 may include alcohol-content information 175a, 175b, and potentially any additional number as illustrated by ellipses 175c for different types of alcohol-containing liquid. For example, alcohol-content information 175a may correspond to an alcohol content of a particular beer, while alcohol-content information 175b corresponds to an alcohol content of a particular vodka. As will be described in more detail to follow, the alcohol-content information of database 175 may be utilized by one or more elements of system 100 to determine the amount of alcohol in the alcohol-containing liquid 115 discharged from the vessel body 111.

As previously mentioned, the system 100 includes the sensing sub-system 120. Although illustrated as a single sensing sub-system, the sensing sub-system 120 may be implemented as multiple sensing devices or sub-systems as circumstances warrant. In an embodiment, the sensing sub-system 120 may include at least one sensing device, such as an alcohol-content sensor 125 that is configured to determine an alcohol content of the alcohol-containing liquid 115. For example, the alcohol content may also be referred to as concentration of alcohol in the alcohol-containing liquid 115, such as percent weight or percent volume of alcohol in the alcohol-containing liquid 115. The alcohol-content sensor 125 may be at least one of a conductivity sensor, a permittivity sensor, a calorimeter, a spectrometer, an acoustic sensor, a specific-gravity sensor, or any other suitable alcohol-content sensor. In such embodiments, the alcohol-content sensor 125 may directly determine the alcohol content in the alcohol-containing liquid 115. Such determination may be made continuously or intermittently based on various measured physical properties of the alcohol-containing liquid 115.

In an embodiment, the sensing sub-system 120 may also include, in addition to the alcohol-content sensor 125, another type of sensing device, such as a weight (or mass or volume) sensor 126 configured to sense data related to the weight of the alcohol-containing liquid 115. In such embodiments, it may be suitable to place sensing sub-system 120 including the weight sensor in the mat device 150 or some other suitable base of the drinking vessel 110 (e.g., on or in a base of the vessel body 111) so as to obtain a more accurate weight measurement. Of course, it will be appreciated that the weight sensor 126 may be placed in other locations if necessary or desired.

In operation, the sensing sub-system 120 including the weight sensor 126 senses the data related to the weight of the alcohol-containing liquid 115 and provides this information to the processor 130 via a wired or wireless connection. In addition, the processor 130 receives the alcohol-content of the alcohol-containing liquid 115 from the alcohol content sensor 125. The processor 130 then calculates the amount of alcohol in the alcohol-containing liquid 115 discharged from drinking vessel 110 using the received data. The processor 130 may be configured to repetitively determine the amount of alcohol based on the received data.

In an embodiment, the weight sensor 126 senses data related to the weight of the alcohol-containing liquid at a first time or time period and then senses additional data at a second or more additional times or time periods. This helps to determine the amount of the alcohol-containing liquid 115 that is discharged and, in turn, helps to determine the amount of alcohol in the discharged alcohol-containing liquid 115. For example, a difference between the amount of the alcohol-containing liquid 115 determined at the second time or time periods based on the weight and the amount of the alcohol-containing liquid 115 determined at the first time or time period based on the weight may be calculated by a weight-sensor processor 127 coupled to the weight sensor via a wired or wireless connection, and the difference may be provided to the processor 130 via a wired or wireless connection. The processor 130 may calculate the amount of alcohol in the alcohol-containing liquid 115 discharged from the vessel body 111 using the difference and the alcohol content received from the alcohol-content sensor 125. In an embodiment, the data sensed by the weight sensor 126 may include data related to the cumulative weight of the drinking vessel 110 and the alcohol-containing liquid 115 at the two or more different times or time periods.

In an embodiment, at least one of an optional inclinometer or accelerator 128 may be coupled to the weight sensor 126 and the weight-sensor processor 127 and configured to sense when the vessel body 111 has been tipped and, consequently, discharged some or all of the alcohol-containing liquid 115. For example, the inclinometer or accelerometer 128 may be used to determine when the drinking vessel 110 has been knocked over and the measured amount of alcohol-containing liquid 115 discharged therefrom is not as a result of human consumption.

As shown in FIG. 1A, in one or more embodiments, the processor 130, which may be any suitable processor, may be operably coupled to the database 175 as illustrated by line 135. Accordingly, the processor 130 is configured to access the alcohol-content information 175a-175b as needed or desired. Thus, in an embodiment, the processor 130 may receive the data related to the weight of the alcohol-containing liquid 115, as discussed previously, from the weight sensor 126. As an alternative or in addition to employing the alcohol-content sensor 125 to determine alcohol content of the alcohol-containing liquid 115, the processor 130 may also access or receive alcohol-content information 175a-175b corresponding to the alcohol-containing liquid 115 from the database 175. For example, if the alcohol-containing liquid 115 were a particular type or brand of beer, then processor 130 may access or receive alcohol-content information corresponding to the type or brand of beer.

In a further embodiment, the sensing sub-system 120 may include, in addition to the alcohol-content sensor 125, a volume sensor (also represented with reference numeral 126) configured to sense data related to the volume of the alcohol-containing liquid 115. In operation, the sensing sub-system 120 including the volume sensor senses the data related to the volume of the alcohol-containing liquid 115 and provides this information to the processor 130. In addition, the processor 130 receives the alcohol-content of alcohol-containing liquid 115 from the alcohol content sensor. The processor 130 then calculates the amount of alcohol in the alcohol-containing liquid 115 discharged from vessel body 111 using the received data. The processor 130 may be configured to repetitively determine the amount of alcohol based on the received data.

In an embodiment, the volume sensor senses data related to the volume of the alcohol-containing at a first time or time period and then senses this data at one or more additional times or time periods. This helps to determine the amount of the liquid 115 that is discharged and, in turn, helps to determine the amount of alcohol in the discharged alcohol-containing liquid 115. For example, the amount of the alcohol-containing liquid 115 determined at the second time or time period based on the volume may be subtracted by the processor 130 from the amount of the alcohol-containing liquid 115 determined at the first time or time period based on the volume.

In one or more embodiments, the processor 130 may receive the data related to the volume of the alcohol-containing liquid 115 or may receive the alcohol content measured by the alcohol-content sensor 125, as discussed above. The processor 130 may also access or receive alcohol-content information 175a-175b corresponding to alcohol-containing liquid 115 as discussed above. The processor 130 may then calculate the amount of alcohol based on the data related to the volume and the received alcohol-content information.

Figure 1B:
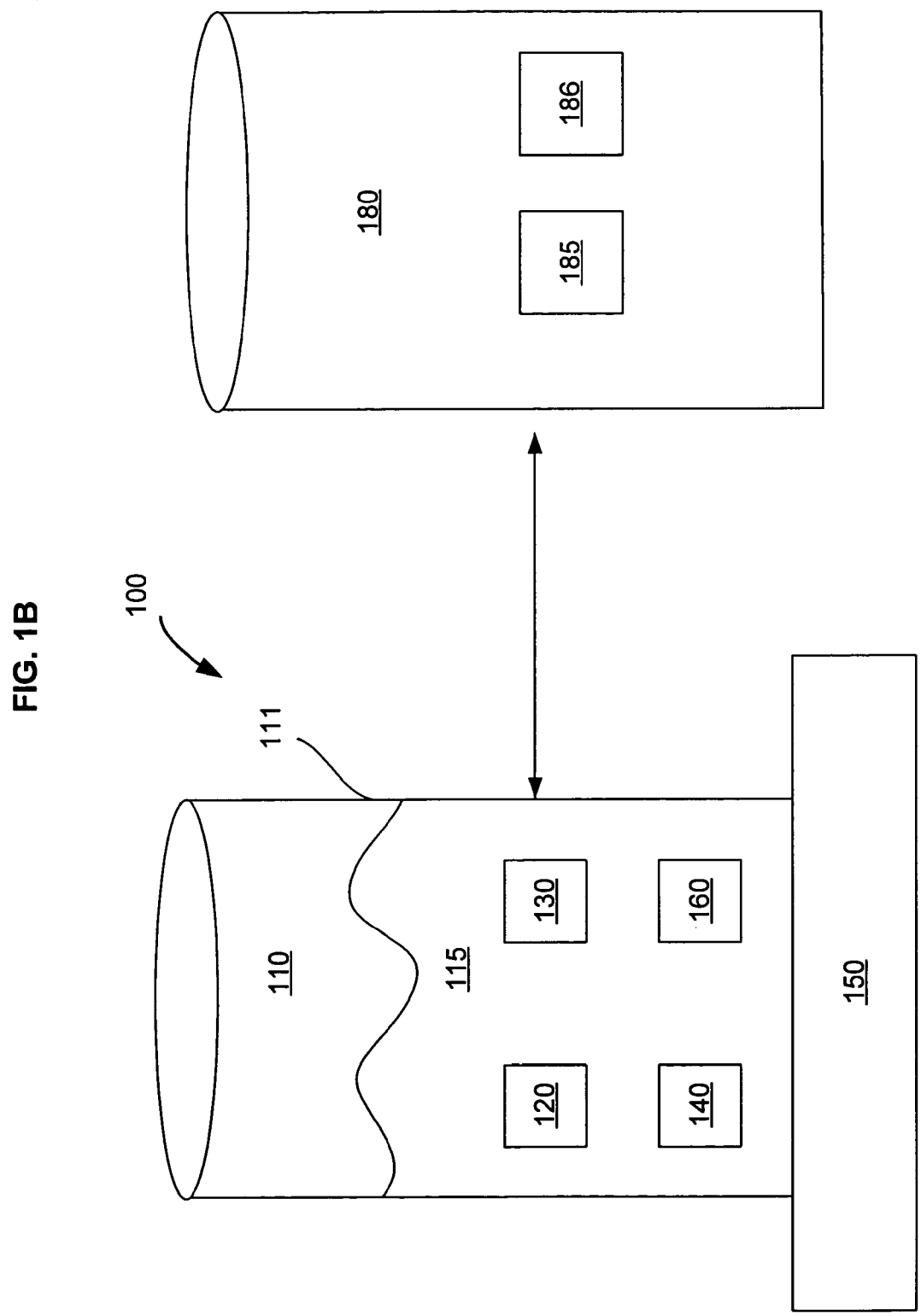
FIG. 1B is a functional block diagram of another embodiment of the system shown in FIG. 1A.

FIG. 1B illustrates a functional block diagram of another embodiment of the system 100. In this embodiment, in addition to elements discussed above in relation to FIG. 1A, the drinking vessel 110 is associated with a reader device 160. In addition, the system 100 includes an alcohol container 180 that holds the alcohol-containing liquid 115 prior to it being poured into drinking vessel 110. The alcohol container 180 may be a bottle, a tap, a keg, or any other suitable alcohol container.

In one embodiment, the reader device 160 may be an optical reader (e.g., a bar-code scanner) configured to read information from a label (e.g., a bar-code label). For example, the alcohol container 180 may include a label 185 that has thereon alcohol-content information for the alcohol-containing liquid 115. In operation, the optical reader 160 may optically scan the alcohol-content information from the label 185. This information may then be provided to processor 130 to use in determining the amount of alcohol in conjunction with the sensing sub-system 120 as previously discussed.

In another embodiment, the reader device 160 may be a radio-frequency-identification-device (RFID) reader configured to receive alcohol-content information. For example, the alcohol container 180 may include a RFID tag 186 that is configured to transmit alcohol-content information for the alcohol-containing liquid 115. In operation, the RFID reader 160 may interrogate the RFID tag 186 to receive the alcohol-content information therefrom, and may then provide this information to the processor 130 to use in determining the amount of alcohol discharged from the vessel body 111 in conjunction with the sensing sub-system 120, as previously discussed.

Returning to FIG. 1A, as discussed previously, the system 100 includes a reporting device 140 configured to report information at least related to an amount of alcohol in the alcohol-containing liquid 115 that has been discharged from vessel body 111. In some embodiments, the amount may be determined by the processor 130 as discussed above.

The reported information at least related to the amount of alcohol in the alcohol-containing liquid 115 discharged from vessel body 111 may be at least one of the amount of the alcohol-containing liquid 115 discharged from vessel body 111, the amount of the alcohol-containing liquid 115 discharged from vessel body 111 and information related to an alcohol content of the alcohol-containing liquid 115, an alcohol content of the alcohol-containing liquid 115, type of the alcohol-containing liquid 115, or other suitable information. For example, the reporting device 140 may report the amount of alcohol in the alcohol-containing liquid 115 discharged based on the readings of the weight or volume sensors previously discussed. As will be appreciated, the reporting device 140 may be configured to report any additional information at least related to an amount of alcohol in the alcohol-containing liquid 115, as needed or desired, for a particular application.

Figure 1C:
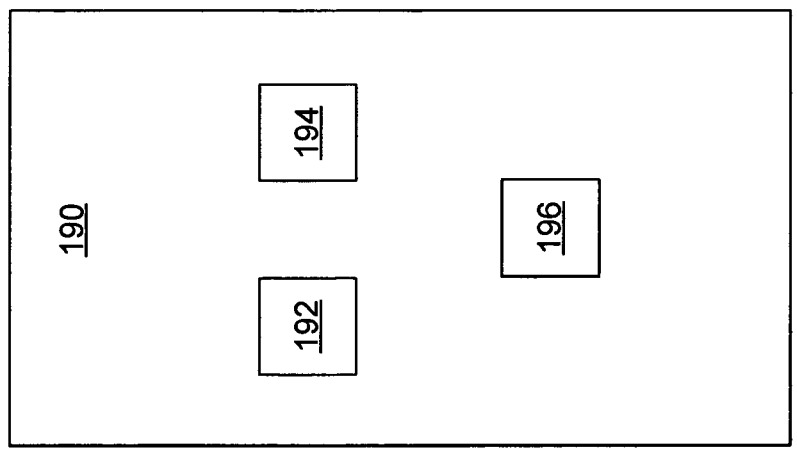
FIG. 1C is a block diagram of an embodiment of a reporting device suitable for use in the systems shown in FIGS. 1A and 1B.

FIG. 1C is a block diagram of an embodiment of a reporting device 190 that may correspond to the reporting device 140 shown in FIGS. 1A and 1B. Although shown as including multiple elements, it will be appreciated that the reporting device 190 may include more or less than the illustrated elements as circumstances warrant.

The reporting device 190 may include a display device 192, which may be any suitable display device. In operation, the display device 192 may be configured to indicate the amount of alcohol-containing liquid 115 or the amount of alcohol that has been discharged from the vessel body 111. For example, the display device may display a first indicium, such as a number or symbol, which shows an amount at a first time or time period as determined by the sensing sub-system 120 or the processor 130. When an amount of liquid or alcohol has been discharged from the drinking vessel 110 at a second time or time period, the display device 192 may change to a different indicium, such as number or symbol, which is indicative of the amount that has been discharged. In an embodiment, the display device 192 may simply display the amount that has been discharged.

In an embodiment, the display device 192 may be configured to display indicia related to a comparison between the amount of liquid or alcohol that has discharged and a reference amount of alcohol-containing liquid or alcohol. For example, the comparison may be performed by the processor 130 or another processor that has access to the amount that has been discharged and to the reference amount. This information may then be provided to reporting device 190, where it may be displayed on display device 192. In an embodiment, the indicia related to the comparison may be a number related to the difference between the discharged amount and the reference amount. In other embodiments, the indicia related to the comparison may be a symbol related to the difference between the discharged amount and the reference amount. In still other embodiments, the indicia related to the comparison may be a number or symbol that indicates how much the amount that has been discharged exceeds the reference amount.

In one or more embodiments, it may be desirable to know a cumulative amount of alcohol-containing liquid or alcohol that has been discharged from vessel body 111. Accordingly, the display device 192 may display a number or symbol that is indicative of the cumulative amount of alcohol or alcohol-containing liquid 115 that has been discharged from vessel body 111. In an embodiment, the cumulative amount may be measured for a single drinker or a single drinking session. The processor 130 or some other processor may determine when to begin to track the cumulative amount and may then determine the cumulative amount in conjunction with sensing sub-system 120 as described. This information may be provided to reporting device 190 and shown on display device 192.

In an embodiment, the display device 192 may include a light source that is configured to change operation in response to the amount of the alcohol-containing liquid 115 or alcohol being discharged from vessel body 111. For example, the light source may be a light-emitting diode (LED) that changed from green to red when a predetermined amount of liquid or alcohol has been discharged. As another example, the light source may begin to blink or will turn off or on when the predetermined amount of the alcohol-containing liquid 115 or alcohol has been discharged.

The reporting device 190 may also include an audio device 194 configured to generate an audio sound or signal indicating the amount of alcohol-containing liquid 115 or alcohol that has been discharged from vessel body 111. In an embodiment, the audio sound may be a voice that states the actual amount that has been discharged. In other embodiments, the audio sound may be a siren-like sound that is activated when a predetermined amount of the alcohol-containing liquid 115 or alcohol has been discharged. It will be appreciated that the audio signal or sound generated by audio device 194 may alert the consumer (drinker), a third party such as a bar tender, spouse, or law-enforcement personnel of the amount of the alcohol-containing liquid 115 or alcohol that has been discharged. Then appropriate steps may be taken to ensure that no harm is caused to or by the drinker of the drinking vessel 110.

The reporting device 190 may also include a transmitter/receiver 196. The transmitter/receiver 196 may receive from an external device (e.g., the sensing sub-system 120 or the processor 130 as described hereinabove) the information regarding the amount of alcohol-containing liquid 115 or the amount of alcohol that has been discharged out of the drinking vessel 110. The reporting device 190 may then report this information as described.

In one or more embodiments, it may be desirable to report the information regarding the amount of alcohol-containing liquid 115 or the amount of alcohol that has been discharged from the drinking vessel 110 to an external device where it may be displayed or affect the operation of the external device. The external device may belong to the consumer (drinker), a third party, such as a bar tender, spouse, or law-enforcement personnel, which may have interest in knowing the amount of alcohol-containing liquid 115 or alcohol that has been discharged. Accordingly, the transmitter/receiver 196 may transmit one or more data signals that encode the information regarding the amount of alcohol-containing liquid 115 or the amount of alcohol that has been discharged to the external device, such as phone, PDA, a computer, iPod®, etc. The data signals may be one or more electromagnetic signals, one or more optical signals, or any combination of electromagnetic and optical signals as circumstances warrant.

FIG. 1D illustrates a functional block diagram of another embodiment of the system 100. As illustrated, the mat device 150 is not present. The processor 130 and the reporting device 140 are also included with the computer 170. Thus, this embodiment shows that the processor 130 and the reporting device 140 need not be integrated with the drinking vessel 110. Although they are shown as part of the computer 170, it will be appreciated that this is for ease of illustration only and that these elements may be integrated with other devices or elements of system 100.

FIGS. 2A-2E illustrate various embodiments of a system 200 that includes a drinking vessel 210 and a mat device 220. The drinking vessel 210 and the mat device 220 may correspond to the drinking vessel 110 and the mat device 150 of the system 100. Accordingly, any discussion relating to a sensing sub-system, a processor, and a reporting device in connection with FIGS. 2A-2E correspond to the operation of like or similar elements previously discussed in relation to system 100.

Figure 2A:
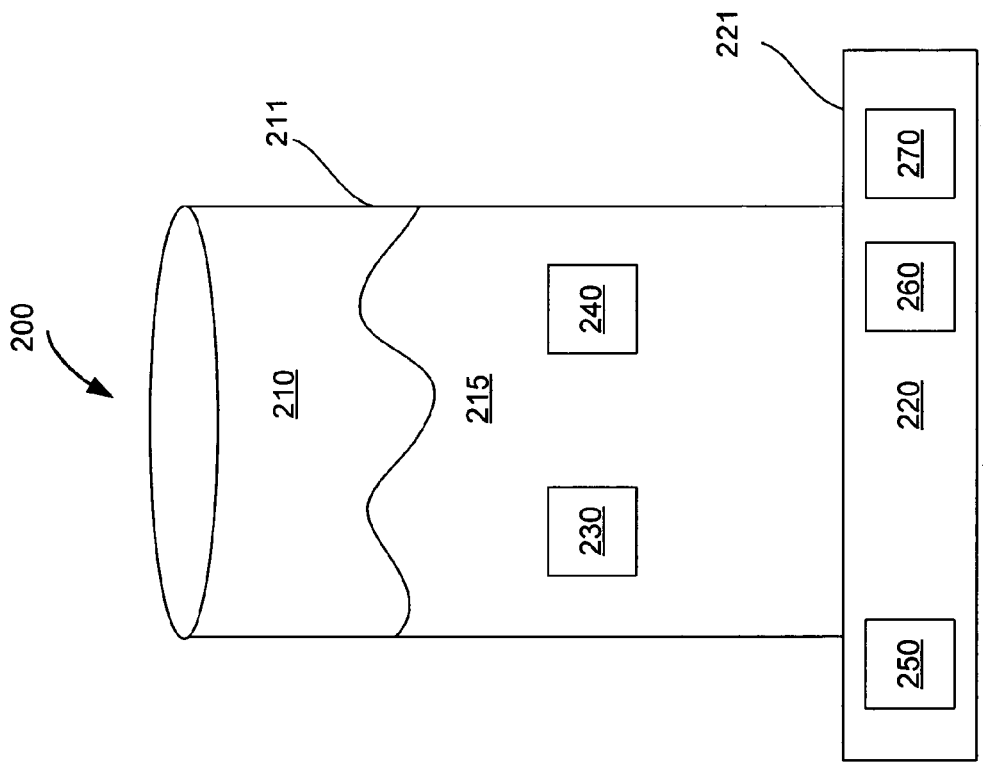
FIGS. 2A-2E are respective functional block diagrams for different system embodiments that include a drinking vessel and a mat device configured to support the drinking vessel.

FIG. 2A illustrates an embodiment of the system 200. The drinking vessel 210 includes a vessel body 211 that contains an alcohol-containing liquid 215. The mat device 220 includes a mat body 221 that is configured to support the drinking vessel 210. In an embodiment, the mat device 220 may be a moveable device that is positionable in multiple locations. In such an embodiment, the mat device 220 may be made of a plastic, a metal, or another suitable material. In other embodiments, the mat device 220 may form at least a part of a support structure. For example, the mat device 220 may be integrated with a counter or table top on which the drinking vessel 210 may be placed. As another example, the mat device 220 may be part of another movable support structure, such as a coaster or a plate.

The mat device 220 may be associated with a sensing sub-system 230, a reporting device 240, and a processor 250. In the illustrated embodiment, the processor 250 is integrated with the mat device 220. In an embodiment, the processor 250 may be embedded into the mat body 221, while in other embodiments the processor 250 may be mounted to a surface of the mat body 221 by any reasonable mounting technique. The sensing sub-system 230 and the reporting device 240 in this embodiment are integrated with the drinking vessel 210. As described above in relation to FIG. 1A, the sensing sub-system 230 may be configured to sense at least one characteristic related to the amount of alcohol or alcohol in the alcohol-containing liquid 215 and the processor 250 may be configured to determine the alcohol-content of alcohol-containing liquid 215 or an amount (e.g., weight, volume, or mass) of the alcohol-containing liquid 215 discharged from the vessel body 211 based on the sensed at least one characteristic. The reporting device 240 is configured to communicate information at least related to the amount of alcohol discharged from the vessel body 211.

In an embodiment, the processor 250 may receive alcohol-content information from an external source, such as the database 175 of the computer 170 (FIG. 1A). In other embodiments, the alcohol-content information may be received from the drinking vessel 210 when this information is determined by the sensing sub-system 230. Accordingly, the mat device 220 may include a receiver 260 that is configured to receive the alcohol-content information from the external source. The receiver 260, which may be any suitable receiver, may then provide this information to the processor 250, and the processor 250 may determine the amount of alcohol in the alcohol-containing liquid 215 that is discharged from the vessel body 211 of the drinking vessel 210.

In further embodiments, the mat device 220 may include a reader device 270, which may be an optical reader (e.g., a bar-code scanner) or an RFID reader. As discussed above in relation to reader device 160, the reader device 270 is configured to read the label of an alcohol container for the alcohol-content information when configured as an optical reader and is configured to receive the alcohol-content information from an RFID tag incorporated with the alcohol container when implemented as an RFID reader.

Figure 2B:
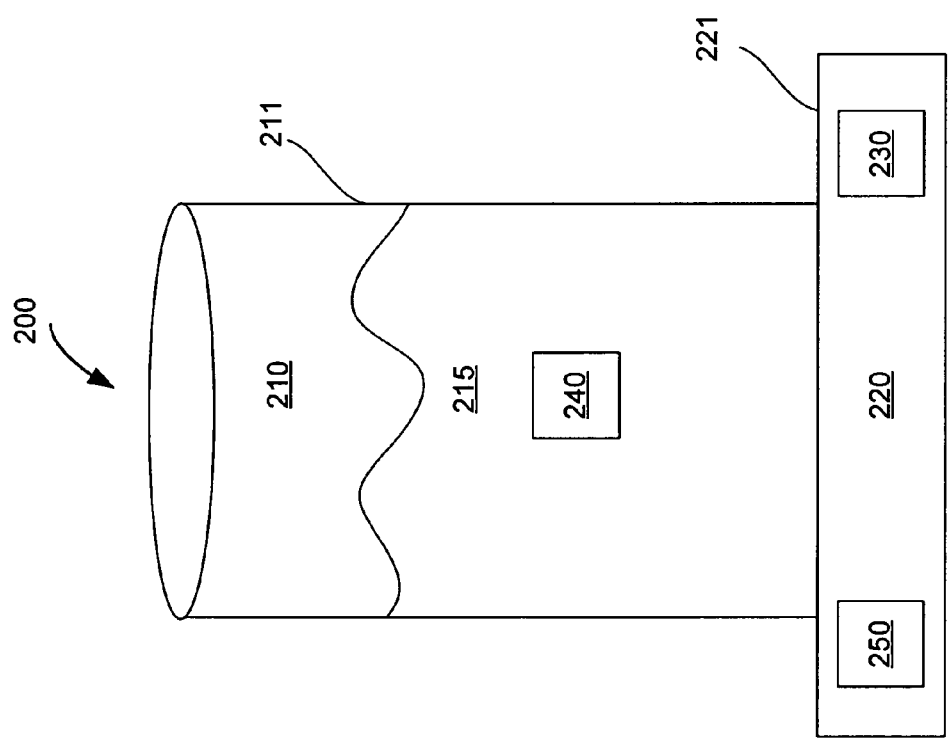

FIG. 2B illustrates another embodiment of the system 200. In this embodiment, the sensing sub-system 230 and the processor 250 are integrated with the mat device 220, while the reporting device 240 is integrated with the drinking vessel 210. It will be appreciated that the sensing sub-system 230 and the reporting device 240 are operably coupled to the processor 250.

In an embodiment, the sensing sub-system 230 may include a weight sensor or a volume sensor. As discussed, the weight sensor is configured to sense data related to the weight (or mass or volume) of the alcohol-containing liquid 215 and the volume sensor is configured to sense data related to the volume of the alcohol-containing liquid 215. The data related to the weight or volume of the alcohol-containing liquid 215 may be related to data taken at two or more times as also previously discussed. It will be appreciated that integrating a sensing sub-system 230 that includes a weight sensor with the mat device 220 may provide for the more accurate weight measurement because the drinking vessel 210 rests on the mat device 220.

Figure 2C:
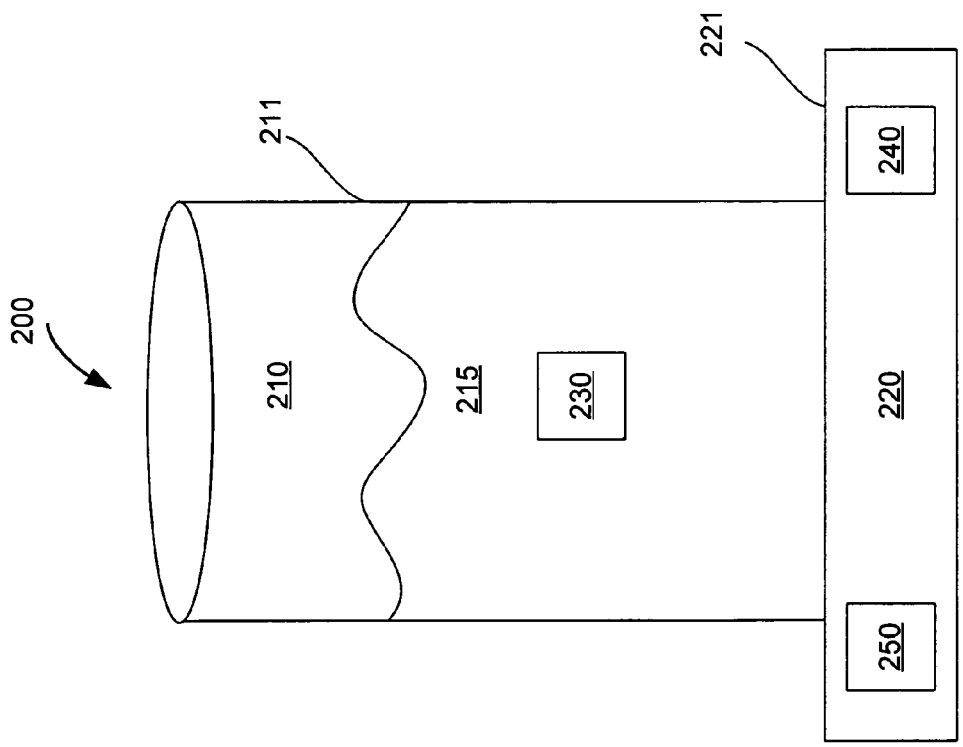

FIG. 2C illustrates a further embodiment of the system 200. In this embodiment, the reporting device 240 and the processor 250 are integrated with the mat device 220, while the sensing sub-system 230 is integrated with the drinking vessel 210. It will be appreciated that the sensing sub-system 230 and the reporting device 240 are operably coupled to the processor 250.

Figure 2D:
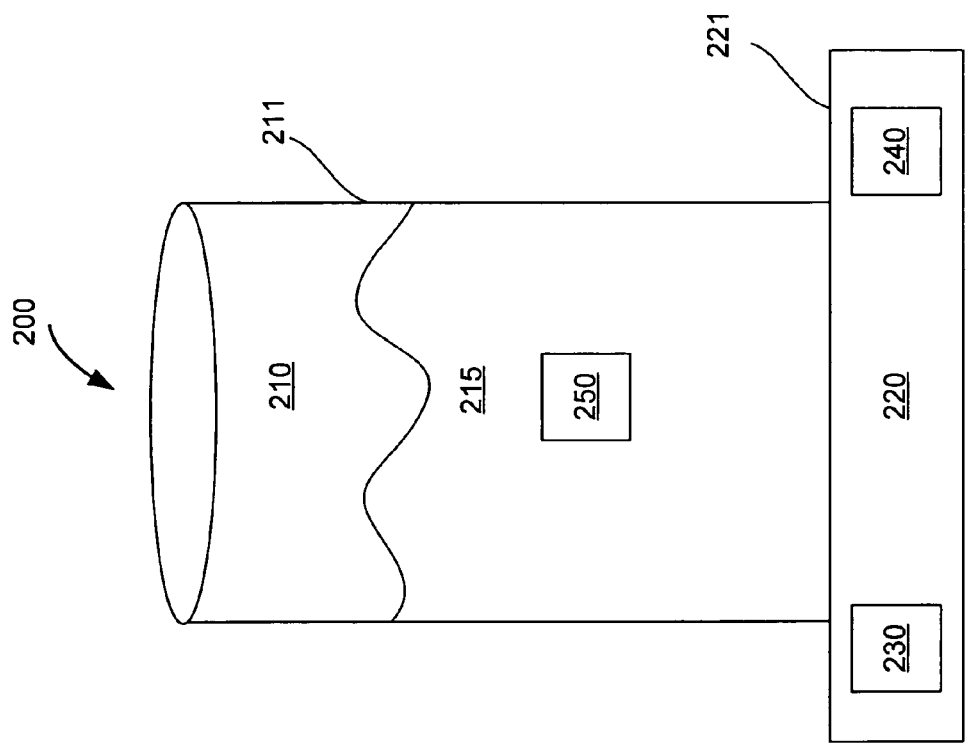

FIG. 2D illustrates an additional embodiment of the system 200. In this embodiment, the sensing sub-system 230 and the reporting device 240 are integrated with the mat device 220, while the processor 250 is integrated with the drinking vessel 210. It will be appreciated that the sensing sub-system 230 and the reporting device 240 are operably coupled to the processor 250.

Figure 2E:
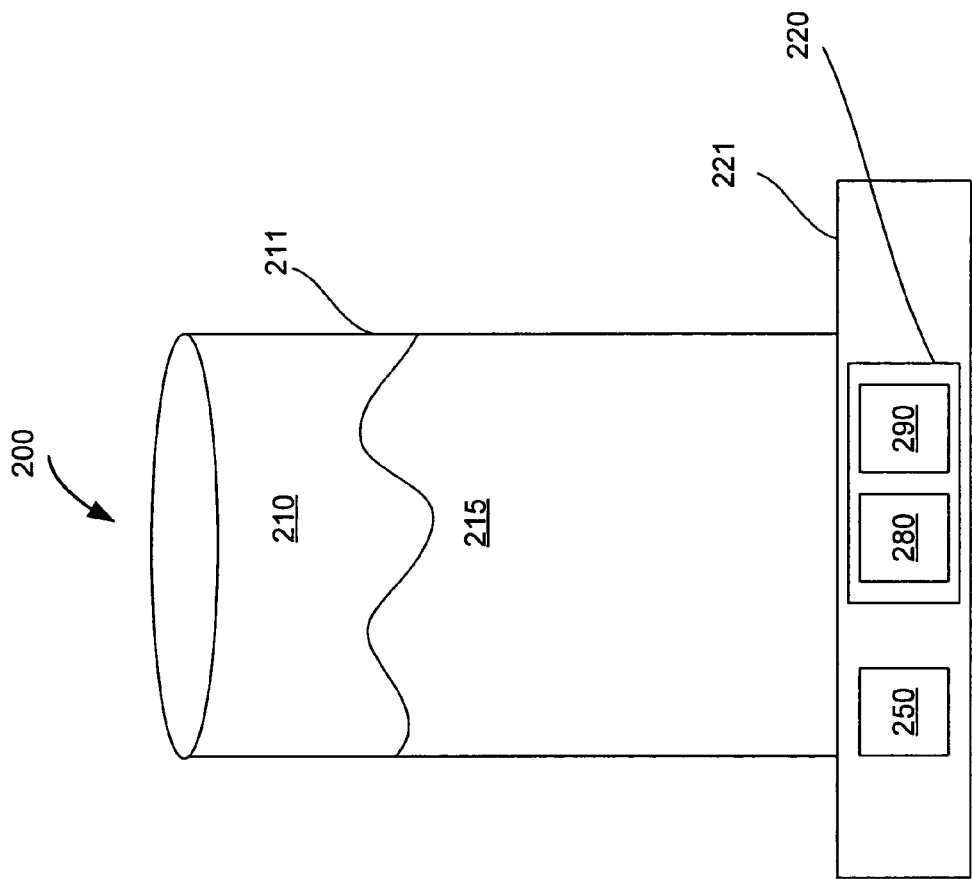

FIG. 2E illustrates yet another embodiment of the system 200. In this embodiment, the mat device includes a sensing sub-system 220 associated with the mat body 221. The sensing sub-system 220 may include a first sensing device 280 configured to measure the amount of the alcohol-containing liquid 215 discharged from the vessel body 211. The sensing sub-system 220 also includes a second sensing device 290 configured to measure an alcohol content in the alcohol-containing liquid 215. For example, the second sensing device 290 may be a spectrometer or acoustic sensor that has optical or acoustic access to the alcohol-containing liquid 215 through the vessel body 211, which may be at least partially optically transparent (e.g., made from a glass) or at least partially acoustically transparent. The processor 250 is configured to calculate the amount of alcohol discharged from the vessel body 111 based on the amount measured by first sensing device 280 and the alcohol content measured by second sensing device 290.

In an embodiment, the first sensing device 280 may be a weight sensor configured to sense data related to a weight of the alcohol-containing liquid 215 discharged from the vessel body 211. In other embodiments, the first sensing device 280 may be a volume sensor associated configured to sense data related to a volume of the alcohol-containing liquid 215 discharged from the vessel body 211. In a further embodiment, the first sensing device 280 may be a mass sensor configured to sense data related to a mass of the alcohol-containing liquid 215 discharged from the vessel body 211. The second sensing device 290 may be a spectrometer, an acoustic sensor, or any other sensor suitable for measuring alcohol content of the alcohol-containing liquid 215.

It will be noted that although the first and second sensing devices 280 and 290 are shown as being integrated with the mat device 220, they may also be integrated with the drinking vessel 210 as circumstances warrant. Further, the reporting device 240 may be integrated with the mat device 220 or the drinking vessel 210.

FIG. 3 is a functional block diagram of a system 300 including at least one device that changes a mode of operation (e.g., disable operation) thereof in response to receiving information related to an amount of alcohol consumed by a drinker. The system 300 includes a drinking vessel 310 that contains an alcohol-containing liquid 315. The drinking vessel 310 may be supported by a mat device 312, although this is not necessary. The drinking vessel 310, the alcohol-containing liquid 315, and the mat device 312 may correspond to like or similar elements previously discussed in relation to FIGS. 1A-1C and FIGS. 2A-2E.

The system 300 also includes an alcohol-sensing system 320 that may be configured to determine at least one characteristic related to an amount of alcohol in the alcohol-containing liquid 315 that has been discharged from a drinking vessel 310. The alcohol-sensing system 320 may also generate alcohol-consumption information 325 based at least partially on the at least one characteristic. The at least one characteristic may be mass, weight, volume, electrical properties, acoustic properties, dielectric properties, or another suitable characteristic of the alcohol-containing liquid 315.

In an embodiment, the alcohol-sensing sub-system 320 may correspond to or include at least one of the sensing sub-system 120 or the processor 130. In addition, the alcohol-sensing system 320 may include a weight or volume sensor. The alcohol-sensing sub-system 320 may be associated with vessel body 311 of the drinking vessel 310 as illustrated, or it may be associated with the mat device 312.

The system 300 also includes a reporting device 330 coupled to the alcohol-sensing sub-system 320. The reporting device 330 may be configured to report the alcohol-consumption information 325. In an embodiment, the alcohol-consumption information 325 indicates that a specific amount of alcohol in the alcohol-containing liquid 315 has been discharged from the drinking vessel 310. For example, the specific amount may correspond to an amount that will cause an average human being to become intoxicated or an amount past a legal limit for operating, for example, a motor vehicle. The alcohol-consumption information 325 may be reported to the device 340 as one or more data signals that may be one or more electromagnetic signals or one or more optical signals. The reporting device 330 may correspond to the reporting device 140, and may be associated with the vessel body 111 of the drinking vessel 310 (as illustrated) or associated with the mat device 312.

The system 300 further includes at least one device 340 including a receiver 345 configured to receive the alcohol-consumption information 325 from the reporting device 330. In response to receiving the alcohol-consumption information 325, the device 340 at least partially changes a mode of operation thereof. For example, a mode-change module 346 may cause the device 340 to operate in a different mode than prior to receiving the information 325. In an embodiment, the mode-change module 346 may also include a processor that calculates the drinker's blood alcohol content (BAC) based on the known weight of the drinker stored in the processor and the received alcohol-consumption information 325. For example, the weight of the drinker may be proved by the drinker or another source, such as the drinker's spouse, bar tender, governmental authority, or other source. In such an embodiment, the mode-change module 346 may change the mode of operation of the device 340 when a specific BAC value is reached.

In one embodiment, the device 340 may be a motorized vehicle, such as an automobile or a motorcycle. In operation, the receiver 345 receives the alcohol-consumption information 325 from reporting device 330 and provides the information to mode-change module 346. The mode-change module 346 may then cause the engine of the automobile or motorcycle to not start. For instance, the mode-change module 346 may disable the ignition system of the automobile or motorcycle when the alcohol-consumption information 325 indicates a specific amount of alcohol has been consumed by the drinker that corresponds to an amount that will cause an average human being to become intoxicated or an amount past a legal limit. As will be appreciated, such action will prevent an intoxicated person from driving.

In an embodiment, the device 340 may be a motorized vehicle, such as an automobile. In operation, the receiver 345 receives the alcohol-consumption information 325 from reporting device 330 and provides the information to mode-change module 346. The mode-change module 346 may then cause the doors of the motorized vehicle to not open. For example, the mode-change module 346 may cause the doors to not unlock or to lock when the alcohol-consumption information 325 indicates a specific amount of alcohol has been consumed by the drinker that corresponds to an amount that will cause an average human being to become intoxicated or an amount past a legal limit. As will be appreciated, such action will also prevent an intoxicated person from driving.

In a further embodiment, the device 340 may be a locking mechanism attached to a table top surface or the mat device 312 that supports the drinking vessel 310. In operation, the receiver 345 receives the alcohol-consumption information 325 from reporting device 330 and provides the information to mode-change module 346. The mode-change module 346 may then cause the locking mechanism to prevent the drinking vessel 310 from being lifted from the support surface on which the drinking vessel is set when the alcohol-consumption information 325 indicates a specific amount of alcohol has been consumed by the drinker that corresponds to an amount that will cause an average human being to become intoxicated or an amount past a legal limit. Consequently, the drinker of the drinking vessel 310 will not be able to drink more of the alcohol-containing liquid 315.

In an additional embodiment, the device 340 may be an alcohol-containing liquid dispensing device, such as a beer or wine tap. In operation, the receiver 345 receives the alcohol-consumption information 325 from reporting device 330 and provides the information to mode-change module 346. The mode-change module 346 may then cause the alcohol-containing liquid dispensing device to cease dispensing the liquid so that no more alcohol-containing liquid is provided to the drinking vessel 310 when the alcohol-consumption information 325 indicates a specific amount of alcohol has been consumed by the drinker that corresponds to an amount that will cause an average human being to become intoxicated or an amount past a legal limit. Consequently, the drinker of the drinking vessel 310 will not be able to drink more of the alcohol-containing liquid 315.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, etc. unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms.

For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A drinking vessel, comprising:
    a vessel body configured to hold an alcohol-containing liquid;
    a sensing system embedded within or mounted to the vessel body, the sensing system including an alcohol-content sensor configured to determine an alcohol content of the alcohol-containing liquid; and
    a processor coupled to the sensing system and programmed to determine a total amount of alcohol in the alcohol-containing liquid discharged from the vessel body based, at least in part, on the alcohol content of the alcohol-containing liquid in the vessel body.

2. The drinking vessel of claim 1, wherein the sensing system is further configured to determine an amount of alcohol in the alcohol-containing liquid discharged from the vessel body based, in part, on the alcohol content.

3. The drinking vessel of claim 1, wherein the sensing system is further configured to repetitively determine an amount of alcohol in the alcohol-containing liquid discharged from the vessel body based, in part, on the alcohol content.

4. The drinking vessel of claim 1, wherein the alcohol-content sensor includes at least one of a conductivity sensor, a permittivity sensor, a calorimeter, a spectrometer, an acoustic sensor, or a specific-gravity sensor.

5. The drinking vessel of claim 1:
    wherein the sensing system includes a weight sensor configured to sense data related to a weight of the alcohol-containing liquid discharged from the vessel body
    wherein the processor is coupled to the weight sensor to receive the data therefrom and configured to determine the amount of alcohol in the discharged alcohol-containing liquid based on the data and the alcohol content determined by the alcohol-content sensor.

6. The drinking vessel of claim 5, wherein the data includes data related to a weight of the alcohol-containing liquid within the vessel body at two or more different times.

7. The drinking vessel of claim 5, wherein the vessel body includes a base, and wherein the weight sensor is disposed on or in the base.

8. The drinking vessel of claim 1, wherein the sensing system includes:
    a weight sensor configured to sense a weight of the alcohol-containing liquid prior to and after discharge of the liquid from the vessel body; and
    a weight-sensor processor coupled to the weight sensor to receive information related to the weight of the liquid prior to and after the discharge of the liquid from the vessel body, and configured to determine the weight of the alcohol-containing liquid discharged from the vessel body, wherein the processor is configured to determine the amount of alcohol in the discharged alcohol-containing liquid based on the weight of the alcohol-containing liquid discharged from the vessel body and the alcohol content determined by the alcohol-content sensor.

9. The drinking vessel of claim 8, further comprising at least one of an inclinometer or an accelerometer coupled to the weight sensor and configured to sense when the vessel body has discharged at least a portion of the alcohol-containing liquid.

10. The drinking vessel of claim 8, wherein the processor is wirelessly coupled to the weight-sensor processor.

11. The drinking vessel of claim 8, wherein the weight-sensor processor is wirelessly coupled to the weight sensor or the processor.

12. The drinking vessel of claim 1, wherein the sensing system includes:
    a volume sensor configured to sense data related to a volume of the alcohol-containing liquid discharged from the vessel body, wherein the processor is coupled to the volume sensor to receive the data therefrom and configured to calculate the amount of alcohol in the discharged alcohol-containing liquid based on the data and the alcohol content determined by the alcohol-content sensor.

13. The drinking vessel of 12, wherein the data includes data related to a volume of the alcohol-containing liquid within the vessel body at two or more different times.

14. The drinking vessel of claim 1, wherein the sensing system includes at least one sensing device configured to measure data related to the amount of the alcohol-containing liquid discharged from the vessel body.

15. The drinking vessel of claim 14, wherein the data includes data related to the amount of the alcohol-containing liquid within the vessel body at two or more different times.

16. The drinking vessel of claim 14, wherein the data includes data related to at least one of a mass of the alcohol-containing liquid discharged from the vessel body or a volume of the alcohol-containing liquid discharged from the vessel body.

17. The drinking vessel of claim 14, wherein the data includes data related to the cumulative weight of the drinking vessel and the alcohol-containing liquid within the vessel body at two or more different times.

18. The drinking vessel of claim 1, further comprising a reporting device operably coupled to the alcohol-sensor device and configured to communicate an amount of alcohol in the alcohol-containing liquid discharged from the vessel body or an amount of the alcohol-containing liquid discharged from the vessel body.

19. The drinking vessel of claim 18, wherein the reporting device is configured to communicate the alcohol content via one or more visible or audio signals.

20. The drinking vessel of claim 18, wherein the reporting device is configured to communicate the alcohol content via one or more electrical or optical signals.

21. A method, comprising:
    sensing, with at least one sensing device, at least one characteristic related to an amount of alcohol in an alcohol-containing liquid that is discharged from a drinking vessel having the at least one sensing device included as part thereof; and
    reporting information associated with the at least one characteristic.

22. The method of claim 21, wherein reporting information associated with the at least one characteristic includes reporting the information to a processor that calculates the amount of alcohol based, at least in part, on the at least one characteristic.

23. The method of claim 21, wherein reporting information associated with the at least one characteristic includes transmitting one or more data signals to another device, the one or more data signals encoding the information.

24. The method of claim 21, wherein reporting information associated with the at least one characteristic includes displaying indicia related to a comparison between the amount that has been discharged to a reference amount of alcohol-containing liquid or alcohol.

25. The method of claim 24, wherein the indicia related to the comparison includes a number related to the difference between the amount that has been discharged and the reference amount.

26. The method of claim 24, wherein the indicia related to the comparison includes a symbol related to the difference between the amount that has been discharged and the reference amount.

27. The method of claim 24, wherein the indicia related to the comparison includes a symbol that indicates the amount that has been discharged has exceeded the reference amount.

28. The method of claim 27, wherein the indicated amount is cumulative with an amount of alcohol-containing liquid or alcohol previously held in the drinking vessel or cumulative with previous alcohol usage.

29. The method of claim 22, wherein the processor is included as part of the drinking vessel.

30. The method of claim 22, wherein the processor is not included as part of the drinking vessel.

31. The method of claim 21, wherein reporting information associated with the at least one characteristic includes displaying the information on a display device.

32. The method of claim 21, wherein reporting information associated with the at least one characteristic includes generating an audible signal when the amount of alcohol exceeds a specified level.

33. The method of claim 21, wherein reporting information associated with the at least one characteristic includes generating a visual signal when the amount of alcohol exceeds a specified level.

34. The method of claim 21, wherein sensing at least one characteristic related to an amount of alcohol in an alcohol-containing liquid that is discharged from a drinking vessel with at least one sensing device includes sensing a quantity of the alcohol-containing liquid discharged from the drinking vessel.

35. The method of claim 28, wherein the quantity is at least one of volume, weight, or mass.

36. The method of claim 21, wherein sensing at least one characteristic related to an amount of alcohol in an alcohol-containing liquid that is discharged from a drinking vessel with at least one sensing device includes:
sensing a quantity of the alcohol-containing liquid contained within the drinking vessel at a first time period;
sensing a quantity of the alcohol-containing liquid contained within the drinking vessel at a second time period that is later than the first time period; and
subtracting the quantity of the second time period from the first time period.

37. The method of claim 21, wherein sensing at least one characteristic related to an amount of alcohol in an alcohol-containing liquid that is discharged from a drinking vessel with at least one sensing device includes sensing an alcohol content of the alcohol-containing liquid discharged from the drinking vessel.

38. The method of claim 21, wherein sensing at least one characteristic related to an amount of alcohol in an alcohol-containing liquid that is discharged from a drinking vessel with at least one sensing device includes receiving information that specifies an alcohol content of the alcohol-containing liquid discharged from the drinking vessel.

39. The method of claim 21, further comprising repetitively calculating the amount of alcohol in the alcohol-containing liquid that is discharged from the drinking vessel using the at least one characteristic.

40. A method, comprising:
sensing, with at least one sensing device, at least one characteristic related to an amount of alcohol in an alcohol-containing liquid that is discharged from a drinking vessel; and
reporting information to a processor that calculates the amount of alcohol based, at least in part, on the at least one characteristic, wherein the processor is included as part of the drinking vessel.

* * * * *